US010265182B2

(12) United States Patent
Foran

(10) Patent No.: US 10,265,182 B2
(45) Date of Patent: *Apr. 23, 2019

(54) ANTIBIOTIC DISPENSING SPACER APPARATUS AND METHOD FOR INFECTED TOTAL KNEE ARTHROPLASTY

(71) Applicant: ForCast Orthopedics, Inc., Longmont, CO (US)

(72) Inventor: Jared Ruben Hillel Foran, Denver, CO (US)

(73) Assignee: ForCast Orthopedics, Inc., Longmont, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/711,507

(22) Filed: Sep. 21, 2017

(65) Prior Publication Data
US 2018/0008423 A1 Jan. 11, 2018

Related U.S. Application Data

(63) Continuation of application No. 15/178,707, filed on Jun. 10, 2016, now Pat. No. 9,839,523.

(51) Int. Cl.
*A61F 2/38* (2006.01)
*A61F 2/30* (2006.01)
*A61F 2/46* (2006.01)

(52) U.S. Cl.
CPC .......... *A61F 2/389* (2013.01); *A61F 2/30771* (2013.01); *A61F 2/3859* (2013.01);
(Continued)

(58) Field of Classification Search
CPC ...... A61F 2002/3068; A61F 2250/0068; A61F 2/389; A61F 2/3859; A61F 2/461; A61F 2002/4615; A61F 2002/30677
See application file for complete search history.

(56) References Cited

U.S. PATENT DOCUMENTS 5,123,927 A 6/1992 Duncan et al.
5,387,240 A 2/1995 Pottenger et al.
(Continued)

FOREIGN PATENT DOCUMENTS

WO 2008/120215 A2 10/2008

OTHER PUBLICATIONS

I. Byren et al., "One hundred and twelve infected arthroplasties treated with 'DAIR'", Journal of Antimicrobial Chemotherapy (2009) 63, 1264-1271, Advance Access publication, Mar. 31, 2009, 8 pgs.
(Continued)

*Primary Examiner* — Alvin J Stewart
(74) *Attorney, Agent, or Firm* — Maier & Maier, PLLC

(57) ABSTRACT

A spacer for a knee replacement prosthesis. The spacer may have a lower surface with a locking component adapted to interlock with a tibial tray, an upper surface optionally with a tibial post and a pair of smooth-surfaced and slightly concave condyle support platforms disposed on opposite sides of the tibial post, and a substantially hollow body with an internal reservoir that can be filled with antibiotic material. The reservoir may be accessible from a port on the hollow body that leads into the internal reservoir, and which permits refilling of the reservoir. In some embodiments, the reservoir may be refillable from this port without removal of the spacer from the patient; for example, a percutaneous needle may be inserted into the port. The spacer may dispense antibiotic from this reservoir to the surrounding area in order to treat an infection.

10 Claims, 6 Drawing Sheets

(52) U.S. Cl.
CPC ...... *A61F 2/461* (2013.01); *A61F 2002/3068* (2013.01); *A61F 2002/30672* (2013.01); *A61F 2002/30878* (2013.01); *A61F 2002/4615* (2013.01); *A61F 2250/0068* (2013.01); *A61F 2250/0098* (2013.01)

(56) References Cited

U.S. PATENT DOCUMENTS

| | | | |
|---|---|---|---|
| 5,891,101 | A | 4/1999 | Wilcox et al. |
| 6,019,794 | A | 2/2000 | Walker |
| 7,090,668 | B1* | 8/2006 | U ........................ A61K 9/0024 604/892.1 |
| 8,454,706 | B2 | 6/2013 | De Beaubien |
| 8,795,242 | B2 | 8/2014 | Hoganson et al. |
| 8,900,322 | B2 | 12/2014 | De Beaubien |
| 8,900,323 | B2 | 12/2014 | de Beaubien |
| 9,561,354 | B2 | 2/2017 | Nebosky et al. |
| 9,839,523 | B1* | 12/2017 | Foran .................. A61F 2/30771 |
| 10,022,233 | B1* | 7/2018 | Gall .................... A61F 2/30771 |
| 2003/0060891 | A1 | 3/2003 | Shah |
| 2003/0187513 | A1 | 10/2003 | Durniak |
| 2005/0015150 | A1 | 1/2005 | Lee |
| 2005/0177118 | A1 | 8/2005 | Hoganson et al. |
| 2006/0093646 | A1 | 5/2006 | Cima et al. |
| 2007/0116734 | A1 | 5/2007 | Akash |
| 2009/0012615 | A1 | 1/2009 | Fell |
| 2009/0069899 | A1 | 3/2009 | Klein |
| 2010/0042167 | A1 | 2/2010 | Nebosky et al. |
| 2010/0042213 | A1 | 2/2010 | Nebosky et al. |
| 2010/0042214 | A1 | 2/2010 | Nebosky et al. |
| 2010/0042215 | A1 | 2/2010 | Stalcup et al. |
| 2010/0204551 | A1 | 8/2010 | Roche |
| 2011/0218644 | A1 | 9/2011 | Meridew et al. |
| 2011/0288642 | A1 | 11/2011 | Forsell |
| 2015/0038899 | A1 | 2/2015 | Tarrant et al. |
| 2015/0038941 | A1 | 2/2015 | Nebosky et al. |
| 2015/0134068 | A1* | 5/2015 | Leonard ................ A61F 2/3886 623/20.27 |
| 2015/0238691 | A1* | 8/2015 | Boyden .................... A61F 2/30 604/66 |
| 2017/0027628 | A1 | 2/2017 | Kim et al. |

OTHER PUBLICATIONS

"Inter Space Knee", URL: https://www.exac.com/products/spacers/interspace-knee, Exactech, Inc., May 5, 2016, 3 pgs.

Fares Sami Haddad FRCS et al., "Is Single-stage Revision According to a Strict Protocol Effective in Treatment of Chronic Knee Arthroplasty Infections?", Clinical Orthopaedics and Related Research, (2015) 473:8-14, Published online: Jun. 13, 2014, 7 pgs.

"StageOne™ Knee Cement Spacer Molds", URL: http://www.biomet.com/wps/portal/internet/Biomet/Home/!ut/p/a1/04_Sj9CPykssy0xPLMnMz0vMAfGjzOL9HA1cDZxMjLzczYltDBw9Qx1D3XxdDE1CjYAKIoEKDHAARwNC-r3QFHgYOgMVOJp5-bi7G1m4mYMsMCrydfZN148qSCzJ0M3MS8vXj_BITcwpyUhOLErVDSjKT0stLs7M1w_XjyJkGkQBHucW5EZU-aQFewIA4PoxbA!!/dl5/d5/L2dBISEvZ0FBIS9nQSEh/, Biomet, Inc., May 5, 2016, 2 pgs.

Susan M. Odum et al., "Irrigation and Debridement for Periprosthetic Infections", The Journal of Arthroplasty vol. 26 No. 6 Suppl. 1 2011, Elsevier Inc., 5 pgs.

S. M. Javad Mortazavi et al., "Two-stage Exchange Arthroplasty for Infected Total Knee Arthroplasty: Predictors of Failure", Clinical Orthopaedics and Related Research, (2011) 469:3049-3054, Published online: Aug. 25, 2011, 6 pgs.

Notification of Transmittal of the International Search Report and the Written Opinion of the International Searching Authority dated Sep. 6, 2017, in connection with corresponding international application No. PCT/US2017/034153 (20 pgs.).

* cited by examiner

ANTIBIOTIC DISPENSING SPACER APPARATUS AND METHOD FOR INFECTED TOTAL KNEE ARTHROPLASTY

CROSS REFERENCE TO RELATED APPLICATIONS

This application claims priority from U.S. patent application Ser. No. 15/178,707, filed on Jun. 6, 2016, entitled "ANTIBIOTIC DISPENSING SPACER APPARATUS AND METHOD FOR INFECTED TOTAL KNEE ARTHROPLASTY", the entire contents of which are hereby incorporated by reference.

BACKGROUND

Though infection is an uncommon complication of arthroplasty, it may have devastating complications, both physical and economic, for a patient and for the healthcare system. Infection following total knee arthroplasty can be difficult to diagnose, and is often difficult to treat once it has been diagnosed. The revision procedure that must be undertaken once an infection has been identified typically involves a combination of surgical debridement to decrease the bacterial bioload as well as revision of one or more components of the prosthesis, and prolonged IV and/or oral antibiotics to eliminate the remaining bacteria. This will mean, for the patient, a longer operating time, greater blood loss, and more chance for other complications to arise, along with increases in the total number of hospitalizations of the patient, their duration of hospitalization, their total number of operations, their total hospital costs, and the total outpatient visits and charges that they must endure.

Currently, several options exist for the treatment of an infected total knee arthroplasty. The first option is simple suppression of the infection with intravenous (IV) and/or oral antibiotics. This option is generally reserved for patients that are thought for any number of reasons to be unfit for surgery. As a general rule, simple IV and/or oral antibiotic treatment of an infected total knee arthroplasty without concomitant surgery is unlikely to result in eradication of an infection, but may suppress the infection such that it is minimally symptomatic.

The second option is a so-called "irrigation and debridement and polyethylene exchange." In this procedure, an open irrigation and debridement of the infected knee is undertaken, with concomitant removal of the polyethylene spacer and placement of a new polyethylene spacer (a "polyethylene exchange"). In some instances, surgeons may elect to add dissolvable antibiotic beads to the knee at the time of surgery. Following this procedure, patients are generally placed on at least 6 weeks of IV antibiotics and may then be put on oral antibiotics for an indefinite period of time. The major advantage to this procedure is that it preserves the current metallic prosthesis, thus minimizing the morbidity of removing a well-fixed prosthesis. Removing a well-fixed prosthesis generally results in loss of variable amounts of native bone stock about the femur and tibia, which is of obvious detriment to the patient. The major disadvantage is that it may be difficult to eradicate the infection using this technique. The success rate for eradication of infection varies a great deal, from 31% to 75%. See, for example, S. M. Odum, T. K. Fehring, & A. V. Lombardi, et al., "Irrigation and debridement for periprosthetic infections: does the organism matter?" 26 J. Arthroplasty 6(suppl):114-118 (2011). See also, for example, I. Byren, P. Bejon, & B. L. Atkins, et al., "One hundred and twelve infected arthroplasties treated with 'DAIR' (debridement, antibiotics and implant retention): antibiotic duration and outcome," 63 J. Antimicrob. Chemother. 1264-1271 (2009).

The third option is a so-called "two-stage exchange." A two-stage exchange consists of two operations. In the first operation, the existing prosthesis and surrounding cement are both removed, a thorough irrigation and debridement is performed, and an antibiotic-eluting polymethylmethacrylate (PMMA) ("bone cement") temporary spacer is placed in place of the prosthesis. Multiple options for a replacement temporary spacer may exist for this procedure. For example, the temporary spacer may be a static spacer, which consists of a block of PMMA that spans the tibiofemoral space and as such holds the knee in a fixed extended position. The temporary spacer may also be of the articulating variety; in this case, the femoral, tibial, and polyethylene parts of the knee are replaced with antibiotic-impregnated molded PMMA components, which may function as a temporary prosthesis, and which may temporarily elute a high, but ever diminishing concentration of antibiotics into the knee. This articulating device allows for some movement of the knee joint. There are several commercially available varieties of PMMA articulating spacers, some of which come pre-formed and pre-loaded with antibiotics (For example, InterSpace Knee, Exactech, Gainesville, Fla.) and some of which are molded by the surgeon in the operating room (For example, Stage One, Zimmer Biomet, Warsaw, Ind.). Additionally, each of these devices aim to temporarily replace the infected prosthesis. That is, the metal femoral and tibial components are removed and replaced with a temporary femoral and tibial drug delivery implant. Following the first stage, in which the existing prosthesis is replaced with a temporary prosthesis, the patient is placed on at least 6 weeks of IV antibiotics. When the infection is thought to be eradicated, the second stage of the procedure is performed. In this stage, the PMMA spacer is removed, and replaced with a revision prosthesis. The advantage of a two-stage procedure is that it has a relatively high success rate, ranging from 72% to 93%. See, for example, S. M. Mortazavi, D. Vegari, A. Ho, B. Zmistowski, & J. Parvizi, "Two-stage exchange arthroplasty for infected total knee arthroplasty: predictors of failure," 469 Clin. Orthop. Relat. Res. 11:3049-54 (November 2011). See also F. S. Haddad, M. Sukeik, & S. Alazzawi, "Is single-stage revision according to a strict protocol effective in treatment of chronic knee arthroplasty infections?" 473 Clin. Orthop. Relat. Res. 1:8-14 (January 2015). The disadvantages are the morbidity of two major operations, potential bone loss caused by removal and reimplanation of the prosthesis, a difficult period for the patient when the antibiotic spacer having restricted functionality is in place, and the high cost of revision implants.

A fourth option is a so-called "one-stage" or "single-stage" exchange. In one-stage exchange arthroplasty, the infected metal prosthesis is removed, the joint is thoroughly irrigated and debrided, and a new revision prosthesis is put in place (often with antibiotic cement for fixation) all in one operation. This is uncommon in the United States for fear of failure. If this approach is undertaken, generally a large amount of tissue and bone are resected, which is a clear disadvantage.

SUMMARY

According to an exemplary embodiment, a spacer for a knee replacement prosthesis may be provided. Such a spacer may include a lower surface, the lower surface having a locking component adapted to interlock with a tibial tray; an upper surface, the upper surface having a pair of condyle support platforms and optionally having a tibial post, each of the condyle support platforms being disposed on an opposite side of the upper surface, each of the condyle support platforms being smooth, the surface of each of the condyle support platforms further having a shallow concavity; and a body, the body having a hollow outer portion surrounding an internal reservoir, the material of the body being impermeable to fluid; the body further having a port with a channel and a flow restrictor, the channel extending through the hollow outer portion of the body, the flow restrictor restricting the flow of fluid in and out of the port in the absence of an external force and permitting the introduction of fluid into the port when an external force is applied.

In another exemplary embodiment, a total knee prosthesis, used to perform a total knee replacement, may be provided. A total knee prosthesis may include a femoral component adapted to be coupled to the distal end of a femur, and having a pair of condyles; a tibial component adapted to be coupled to the proximal end of a tibia, and having a tibial tray; and a spacer, the spacer having a lower surface, the lower surface having a locking component adapted to interlock with the tibial tray; an upper surface, the upper surface having a pair of condyle support platforms and optionally having a tibial post, each of the condyle support platforms being disposed on an opposite side of the upper surface, each of the condyle support platforms being smooth, the surface of each of the condyle support platforms further having a shallow concavity; and a body, the body having a hollow outer portion surrounding an internal reservoir, the material of the body being impermeable to fluid; the body further having a port having a channel and a flow restrictor, the channel extending through the hollow outer portion of the body, the flow restrictor restricting the flow of fluid in and out of the port in the absence of an external force and permitting the introduction of fluid into the port when an external force is applied; wherein the locking component of the spacer is connected to the tibial tray of the tibial component, and wherein each of the condyles of the femoral component is disposed in one of the condyle support platforms of the spacer.

In another exemplary embodiment, a method for adding fluid to a spacer for a knee prosthesis may be provided. The spacer may include a lower surface, the lower surface having a locking component adapted to interlock with a tibial tray; an upper surface, the upper surface having a pair of condyle support platforms and optionally having a tibial post, each of the condyle support platforms being disposed on an opposite side of the upper surface, each of the condyle support platforms being smooth, the surface of each of the condyle support platforms further having a shallow concavity; and a body, the body having a hollow outer portion surrounding an internal reservoir, the material of the body being impermeable to fluid; the body further having a port having a channel and a flow restrictor, the channel extending through the hollow outer portion of the body, the flow restrictor restricting the flow of fluid in and out of the port in the absence of an external force and permitting the introduction of fluid into the port when an external force is applied. The method of adding fluid to said spacer may include applying an external force to the port; inserting a hollow tube into the port; and inserting fluid into the port via the hollow tube. Such a method may be performed percutaneously or otherwise, for example to initially fill the spacer.

BRIEF DESCRIPTION OF THE DRAWINGS

Advantages of embodiments of the present invention will be apparent from the following detailed description of the exemplary embodiments. The following detailed description should be considered in conjunction with the accompanying figures in which.

DETAILED DESCRIPTION

Aspects of the present invention are disclosed in the following description and related figures directed to specific embodiments of the invention. Those skilled in the art will recognize that alternate embodiments may be devised without departing from the spirit or the scope of the claims. Additionally, well-known elements of exemplary embodiments of the invention will not be described in detail or will be omitted so as not to obscure the relevant details of the invention.

As used herein, the word "exemplary" means "serving as an example, instance or illustration." The embodiments described herein are not limiting, but rather are exemplary only. It should be understood that the described embodiments are not necessarily to be construed as preferred or advantageous over other embodiments. Moreover, the terms "embodiments of the invention", "embodiments" or "invention" do not require that all embodiments of the invention include the discussed feature, advantage or mode of operation.

According to at least one exemplary embodiment, and referring generally to the Figures, an antibiotic dispensing spacer to be used in an infected total knee arthroplasty revision procedure may be shown and described. The antibiotic dispensing spacer may directly introduce antibiotics into an infection site at a controlled rate, and may rely on an antibiotic supply that may be replenishable without a need for surgery to remove and replace the device. The antibiotic dispensing spacer may also be shaped and configured so as not to interfere with the function of the knee joint of the patient. Such a spacer may create a new option for the treatment of periprosthetic knee infection, combining many of the benefits of the treatments of the previous options and eliminating many of the drawbacks inherent in said treatments.

Figure 1:
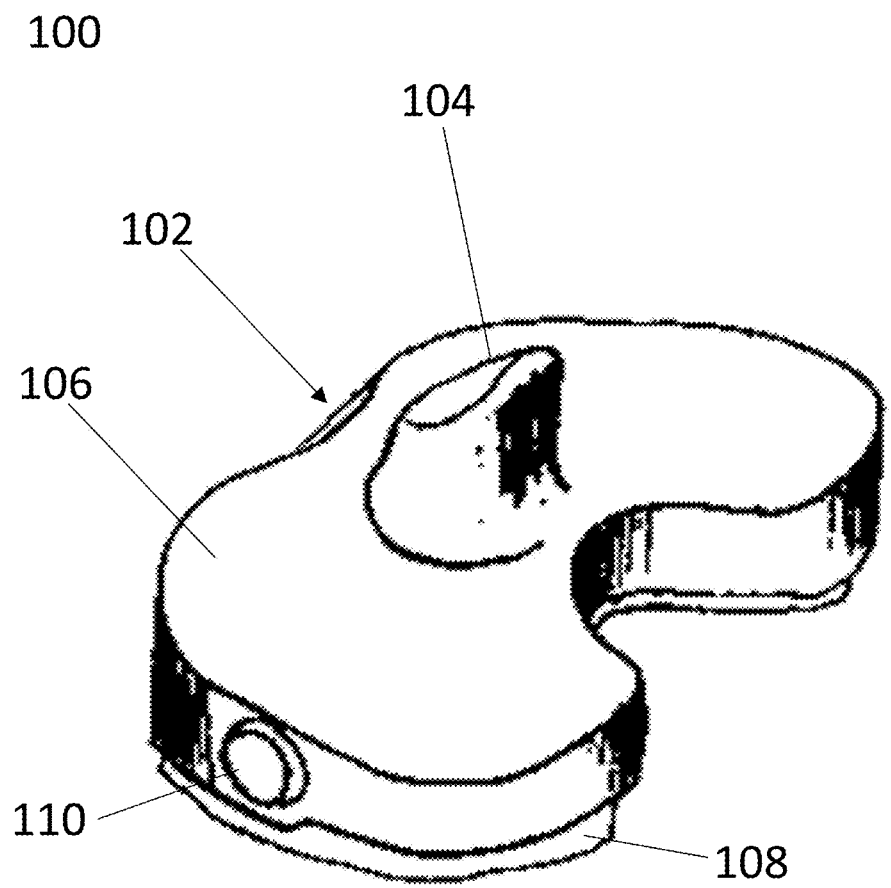
FIG. 1 is an exemplary embodiment of an antibiotic dispensing spacer.

FIG. 1 may depict an exemplary embodiment of an antibiotic dispensing spacer 100, which may be used in a total knee arthroplasty revision procedure. According to an exemplary embodiment, antibiotic dispensing spacer 100 may be adapted to fit between a femoral component of a knee replacement prosthesis and a tibial component of a knee replacement prosthesis, and may be configured to replace or be temporarily substituted for an existing spacer. According to an exemplary embodiment, antibiotic dispensing spacer 100 may fit atop a tibial component of a knee replacement prosthesis, and may be attached to the tibial component by, for example, an adhesive or a physical connector.

Antibiotic dispensing spacer 100 may include a hollow outer shell 102. The upper surface 106 of the antibiotic dispensing spacer 100 may be smooth, and the lower surface 108 of the antibiotic dispensing spacer 100 may include one or more attachment sites at which the antibiotic dispensing spacer 100 can be attached to a tibial component of a knee replacement prosthesis. Antibiotic dispensing spacer 100 may also include one or more ports 110 extending through the hollow outer shell 102 into one or more internal reservoirs located within the antibiotic dispensing spacer 100. Ports 110 may include, for example, a channel portion extending through the hollow outer shell 102 and a flow restrictor portion preventing the flow of fluid in and out of the hollow outer shell 102 when not desired. In some embodiments, antibiotic dispensing spacer may have a tibial post 104 protruding from the top of the spacer 100.

According to an exemplary embodiment, the hollow outer shell 102 of the antibiotic dispensing spacer 100 may be constructed from a material that is biocompatible, and such that there is a low coefficient of friction between the material of the antibiotic dispensing spacer 100 and the material of the femoral component of the knee replacement prosthesis that is in contact with the upper surface 106 of the antibiotic dispensing spacer 100. For example, according to an exemplary embodiment, the hollow outer shell 102 of the antibiotic dispensing spacer 100 may be constructed from polyethylene, carbon composite, or from another appropriate biocompatible material or combination of materials, as desired.

According to an exemplary embodiment, hollow outer shell 102 of the antibiotic dispensing spacer 100 may be formed in any of a variety of shapes and sizes. According to an exemplary embodiment, spacers 100 may be constructed in each of a variety of shapes and sizes, for example the shapes and sizes of the most common commercially available total knee prosthesis spacers, or the shapes and sizes of the total knee prosthesis spacers sold by a particular company. This may allow the spacers 100 to be used for different patients or for different techniques; for example, according to an exemplary embodiment, there may be spacer 100 designs that are intended to be used for posterior stabilized total knee replacement, and spacer 100 designs that are intended to be used for cruciate retaining total knee replacement, or cruciate sacrificing knee replacement, or any other types of knee replacement, as desired. Fixed-bearing spacers 100 and rotating platform/mobile bearing spacers 100, as well as any other spacer 100 designs, may also be available, as desired. According to another exemplary embodiment, spacers 100 may be modular in shape, or may be moldable or otherwise modifiable. For example, according to an exemplary embodiment, a spacer 100 may be become soft and pliable after being exposed to a particular chemical or being exposed to heat, and may be modifiable in such a form.

According to an exemplary embodiment, the upper surface 106 of the antibiotic dispensing spacer 100 may be smooth, and may be shaped so as to accommodate a femoral component of a knee replacement prosthesis. For example, according to an exemplary embodiment, the upper surface 106 may be substantially flat or substantially curved, as desired. For example, according to an exemplary embodiment, the upper surface 106 may have two concave portions, one on either side of the antibiotic dispensing spacer 100 and separated by a tibial post 104. Each of the concave portions may be used to, for example, accommodate the condyles of the femoral component, such that each of the condyles of the femoral component fits within one of the concave portions.

According to an exemplary embodiment, an antibiotic dispensing spacer 100 may have a tibial post 104, which may extend upwards from the upper surface 106 of the antibiotic dispensing spacer 100. According to an exemplary embodiment, in a "posterior-stabilized" or "cruciate-substituting" prosthesis design, the tibial post 104 may be used to prevent posterior translation of the tibia on the femur, helping to stabilize the knee in the absence of the posterior cruciate ligament (PCL). This may allow the antibiotic dispensing spacer 100 to be substituted for an existing spacer of a "posterior-stabilized" or "cruciate-substituting" prosthesis. Other prosthesis variants, such as a "cruciate-retaining" prosthesis, may not include a tibial post 104, and may be used when the patient's PCL can be retained; in such a case, an antibiotic dispensing spacer 100 may be similar in structure to the spacer of a cruciate-retaining design, and may not include a tibial post 104.

According to an exemplary embodiment, the lower surface 108 of the antibiotic dispensing spacer 100 may be connectible, for example by the use of a locking mechanism, to the top portion of a tibial component of a knee replacement prosthesis (known as the "tibial tray"). According to an exemplary embodiment, the antibiotic dispensing spacer 100 may be of a fixed-bearing or rotating platform/mobile bearing design. For example, in one exemplary embodiment, the antibiotic dispensing spacer 100 may have a fixed-bearing design; in such an embodiment, the lower surface 108 may be rigidly attached, for example by a rigid connector or an adhesive, to the tibial component of the knee replacement prosthesis. According to another exemplary embodiment, the antibiotic dispensing spacer 100 may have a rotating platform design; in such an embodiment, the lower surface 108 may be able to rotate back and forth by several degrees on the tibial component of the knee replacement prosthesis.

The hollow outer shell 102 of the antibiotic dispensing spacer 100 may contain one or more reservoirs, which may be accessible from the outside of the antibiotic dispensing spacer 100 by one or more ports 110. For example, in one exemplary embodiment, the spacer 100 may have a port 110 on the anterior, medial or lateral aspects of the spacer 100 which leads to an internal reservoir. According to an exemplary embodiment, port 110 may be protuberant from the surface of the spacer 100, which may, for example, facilitate palpation of the port by an administrating physician. According to another exemplary embodiment, port 110 may not be protuberant, and may instead be a window in the anterior, medial, or lateral aspect of the spacer 100; such a window-type port 110 may be flush with or sunk into the hollow outer shell 102 of a spacer 100, as desired.

In an embodiment, port 110 may be refilled after the spacer 100 is in place, by the application of a percutaneous needle. An administrating physician may insert the needle through the skin of the patient and into the port 110 of the spacer 100, thereby allowing access to an internal reservoir of the spacer 100 and allowing the spacer 100 to be refilled via the needle, for example with the use of a syringe. According to an exemplary embodiment, the port 110 may be made of rubber or another flexible material, or alternatively may be made of a sponge or fibrous material, such that a needle can be inserted through the port 110 and into an internal reservoir without significantly compromising the ability of the port 110 to retain fluid material in the reservoir. According to another exemplary embodiment, the port 110 may be flexibly held in place by the spacer 100, such that the application of a force to the port 110, with a needle or other tool, can open the port 110 and allow for an internal reservoir of the spacer 100 to be refilled via a needle. For example, in an exemplary embodiment, the port 110 may be constructed from a hard material and may be spring-loaded or otherwise held in place by elastic material. In another exemplary embodiment, the internal reservoir may have a structure capable of retaining fluid without requiring a port 110 to act as a barrier; for example, according to an exemplary embodiment, the internal reservoir may be filled with a sponge, such as a hydrophobic or hydrophilic sponge, and fluid may be injected directly into the sponge. According to such an embodiment, port 110 may be, for example, an opening in the hollow outer shell 102 of the spacer 100 allowing insertion of a needle into the internal reservoir.

According to another exemplary embodiment, the port 110 may be connected to a catheter. Catheter may be linked to a refill mechanism, and may be connected to the reservoir of the spacer 100 by percutaneously tunneling the catheter through the soft tissue of the patient's thigh to the reservoir of the spacer 100. Refill of an internal reservoir of the spacer 100 may then take place through this catheter. According to an exemplary embodiment, a catheter, or a port 110 that allows both addition of and removal of antibiotic fluid, may be used in order to allow antibiotic fluid to be drawn out of the spacer 100 as well as added to the spacer 100; this may allow for antibiotic fluid levels or concentrations in the spacer 100 to be more easily checked. Other fluids other than antibiotic fluid may also be added or removed, for example through the port 110 and/or the catheter; for example, in one exemplary embodiment, anticoagulants may be added to prevent clogging of the pores, while in another exemplary embodiment, chemical surfactants may be added to help break down biofilm on the prosthesis.

According to an exemplary embodiment, the port 110 may have a localization marking that allows the port 110 to be localized on X-ray or fluoroscopy. For example, according to an exemplary embodiment, the port 110 may be surrounded by a radiodense ring that allows the port 110 to be observed in an X-ray. According to another exemplary embodiment, such as when the port 110 is constructed from a hard material, the port 110 itself may be constructed from a radiodense material.

Figure 2:
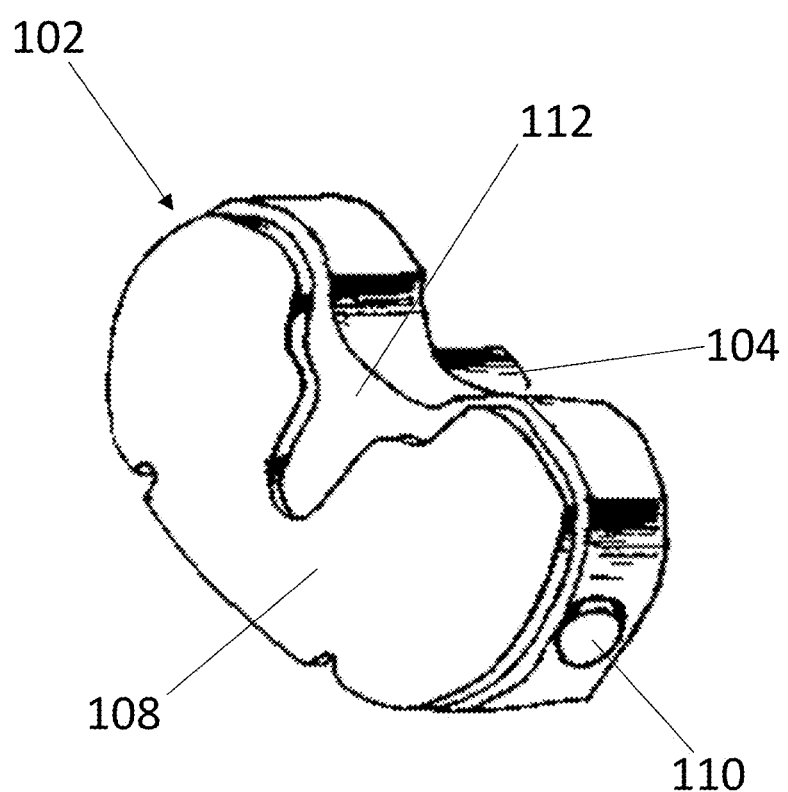
FIG. 2 is a view of the underside of an exemplary embodiment of an antibiotic dispensing spacer.

Turning now to exemplary FIG. 2, FIG. 2 shows a view of the underside of an exemplary embodiment of an antibiotic dispensing spacer 100. According to an exemplary embodiment, the lower surface 108 of the antibiotic dispensing spacer 100 may include a locking mechanism 112 or other mechanical connector by which the antibiotic dispensing spacer 100 can be connected to a tibial tray. For example, according to an exemplary embodiment, a spacer 100 may slide onto an upraised portion of the tibial tray, which may extend into and lock inside the locking mechanism 112. As previously mentioned, according to an exemplary embodiment, the antibiotic dispensing spacer 100 may be of a fixed-bearing or rotating platform/mobile bearing design. According to an exemplary embodiment, locking mechanism 112 may be a duplicate of the locking mechanisms of one or more other commercially available spacers. According to another exemplary embodiment, locking mechanism 112 may be modular or may be modifiable, such that the locking mechanism 112 can be affixed to different tibial tray models or mechanisms. In another exemplary embodiment, the antibiotic dispensing spacer 100 may be connected to a tibial tray by a nonmechanical connection, or a combination of mechanical and nonmechanical connections; for example, in an exemplary embodiment, the antibiotic dispensing spacer 100 may be connected to the tibial tray by an adhesive, by grout/bone cement, or by any other nonmechanical connection, as desired.

Figure 3:
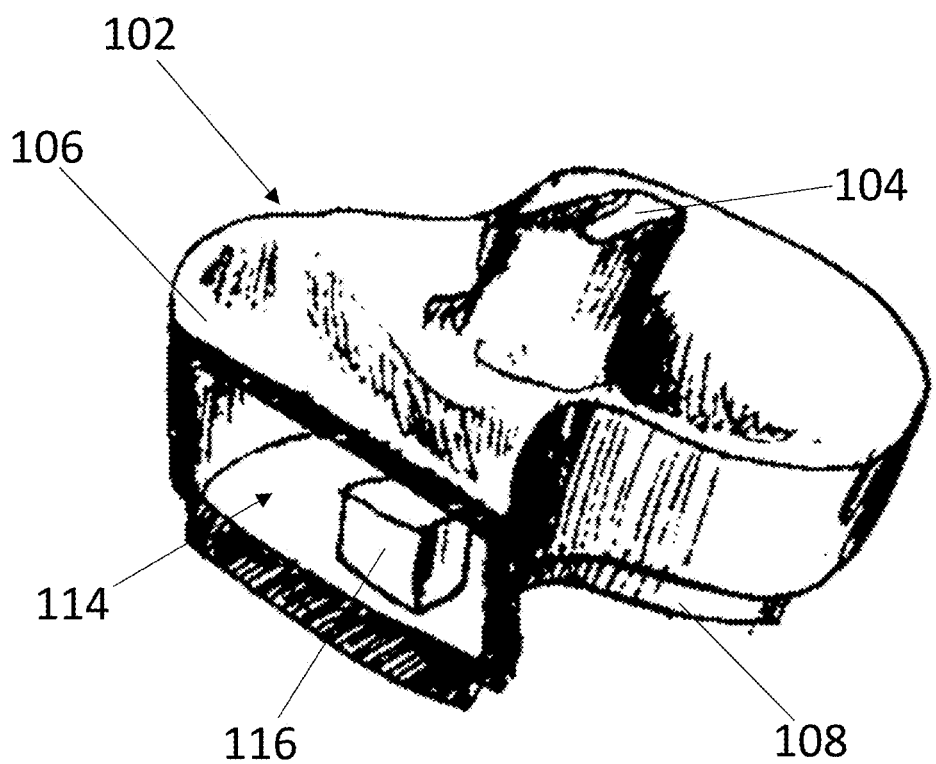
FIG. 3 is a view of the inside of an exemplary embodiment of an antibiotic dispensing spacer.

Turning now to exemplary FIG. 3, FIG. 3 shows a view of the inside of an exemplary embodiment of an antibiotic dispensing spacer 100. The internal portion of an antibiotic dispensing spacer 100 may include, within the hollow outer shell 102, one or more internal reservoirs 114. According to an exemplary embodiment, internal reservoirs 114 may be refillable from the outside; for example, internal reservoirs 114 may be refillable from a port located on the antibiotic dispensing spacer 100 and extending through the hollow outer shell 102.

According to an exemplary embodiment, the one or more internal reservoirs 114 may hold one or more fluids, which may be, for example, solutions of antibiotics, anticoagulants, surfactants, other fluids, or some combination thereof. The one or more internal reservoirs 114 may also be linked to a dispensation mechanism for the fluids, which may act to dispense the fluid in a controlled fashion. For example, according to an exemplary embodiment, the antibiotic dispensing spacer 100 may include one or more pumps, such as pump 116. Pump 116 may be powered by, for example a battery located within the antibiotic dispensing spacer 100 or by another power source, as desired. Pump 116 may be connected to one or more pores or portals located on the hollow outer shell 102 of the spacer 100 and may act to dispense antibiotic-containing fluid out of the one or more internal reservoirs 114 of the spacer 100.

Figure 4:
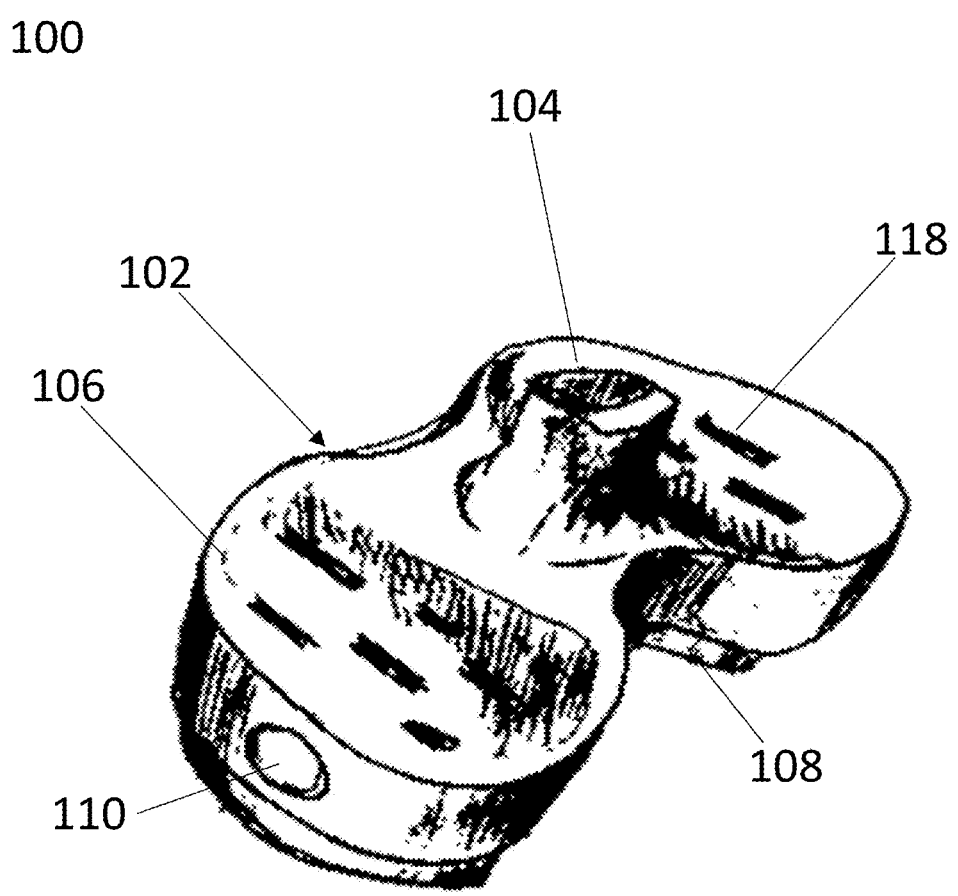
FIG. 4 is an exemplary embodiment of an antibiotic dispensing spacer having a number of pores.

Turning now to exemplary FIG. 4, FIG. 4 shows an alternative exemplary embodiment of an antibiotic dispensing spacer 100, in this case showing, visibly, a plurality of pores 118 that may be located on the hollow outer shell 102 of the spacer 100. According to an exemplary embodiment, pores 118 may allow for antibiotic-containing fluid to be dispensed from an internal reservoir of the spacer 100 by the action of a pump located within the spacer 100. According to another exemplary embodiment, the pores 118 may allow simple diffusion of a liquid located within the spacer 100 to the surrounding joint, without requiring the action of a pump to dispense liquid out of the pores 118. In some exemplary embodiments, pores 118 may be constructed from or may incorporate fluid-permeable material, such as a fluid-permeable membrane; according to such an embodiment, the fluid-permeable material may restrict the rate at which antibiotic-containing fluid is dispensed into the surrounding joint. In other exemplary embodiments, pores 118 may be openings in the hollow outer shell 102 of the spacer 100 that extend through the hollow outer shell 102 of the spacer 100 and into one or more internal reservoirs. Pores 118 may be any size or shape, and may be provided in any number, as desired. In some exemplary embodiments, one or more pores 118 may double as a port into which additional antibiotic-containing fluid can be injected, as desired. In some exemplary embodiments, the hollow outer shell 102 may be slightly permeable to fluid; in such embodiments, no pores may be necessary, and the slight permeability to fluid of the hollow outer shell 102 may instead be used to diffuse liquid located within the spacer 100.

Figure 5:
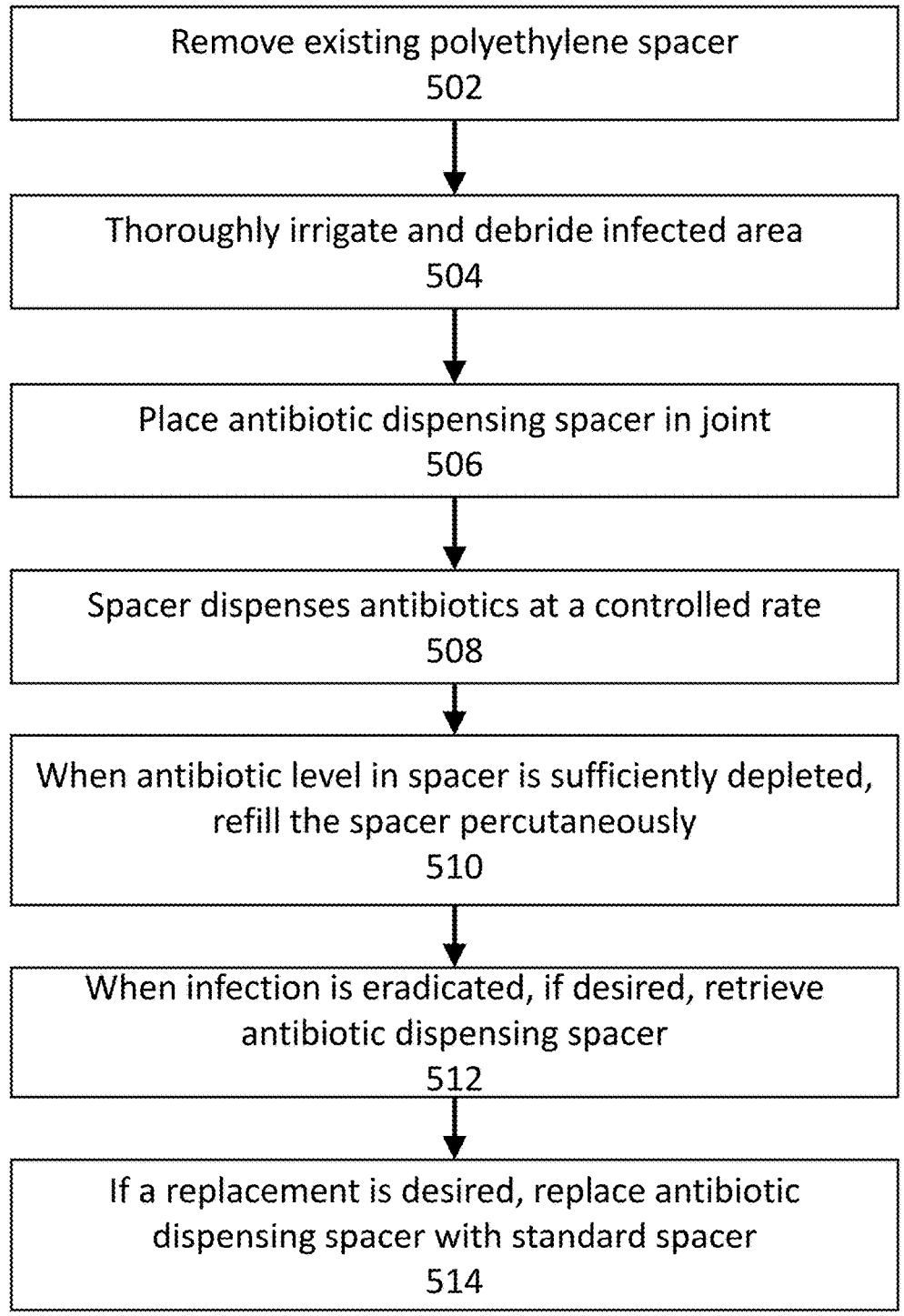
FIG. 5 is an exemplary process flow diagram depicting a method by which an antibiotic dispensing spacer may be used to treat an infection.

Turning now to exemplary FIG. 5, an exemplary process flow diagram depicting a method by which an antibiotic dispensing spacer may be used to treat an infection may be depicted. Once an infection in a total knee replacement prosthetic has been diagnosed, in a first operation, a standard polyethylene spacer may be removed from the knee replacement prosthetic 502. The infection site may then be thoroughly irrigated and debrided in order to remove infected tissue 504. Once the irrigation and debridement 504 is finished, an antibiotic dispensing spacer having one or more internal reservoirs and having a shape similar to or identical with the standard polyethylene spacer removed from the knee replacement prosthetic may be selected, and if necessary may be further reshaped; for example, modular components may be exchanged for other modular components, or the antibiotic dispensing spacer may be modified or remolded. The one or more internal reservoirs of the antibiotic dispensing spacer may be filled with one or more antibiotics, and the antibiotic dispensing spacer may be put inside the knee replacement prosthetic in place of the standard polyethylene spacer 506.

Once the antibiotic dispensing spacer is put in place, it may be left in place for an extended period of time, such as 6-8 weeks, or however long it may take for the infection to have been satisfactorily treated. During that time, the antibiotic dispensing spacer may dispense antibiotics, for example using a pump or using diffusion, into the knee area at a controlled rate 508. Alternatively, in an exemplary embodiment, the antibiotic dispensing spacer may be left in place permanently, which may, for example, simplify the process of treating a recurrence of the infection. Alternatively, in another exemplary embodiment, the antibiotic dispensing spacer may be added preemptively, before an infection occurs, in order to simplify the process of treating the infection and reduce the need for further surgeries after the prosthesis is initially put in place.

At one or more instances within the time period in which the antibiotic dispensing spacer is in place, the antibiotic dispensing spacer may become depleted past a desirable point. For example, the reservoirs of the antibiotic dispensing spacer may become fully depleted, or sufficiently depleted that the amount of antibiotic being dispensed by the antibiotic dispensing spacer are near a minimum desirable amount or less than a minimum desirable amount. At that point, the spacer may be refilled percutaneously 510, for example by the injection of a syringe into a port of the spacer or the insertion of a catheter into a port of the spacer. This may allow for the antibiotic dispensing spacer to be refilled without requiring the full surgical removal and replacement of the empty antibiotic dispensing spacer with a filled antibiotic dispensing spacer, which may result in easier maintenance of antibiotic levels and greatly reduced inconvenience for the patient.

Once the infection has been deemed to be eradicated, the antibiotic dispensing spacer may be retrieved 512, and may be replaced with a standard spacer 514, if desired. Standard spacer may be, for example, the spacer that was initially removed from the infected total knee replacement, or may be another spacer, as desired. Alternatively, as mentioned, the antibiotic dispensing spacer may be left in place permanently.

Figure 6:
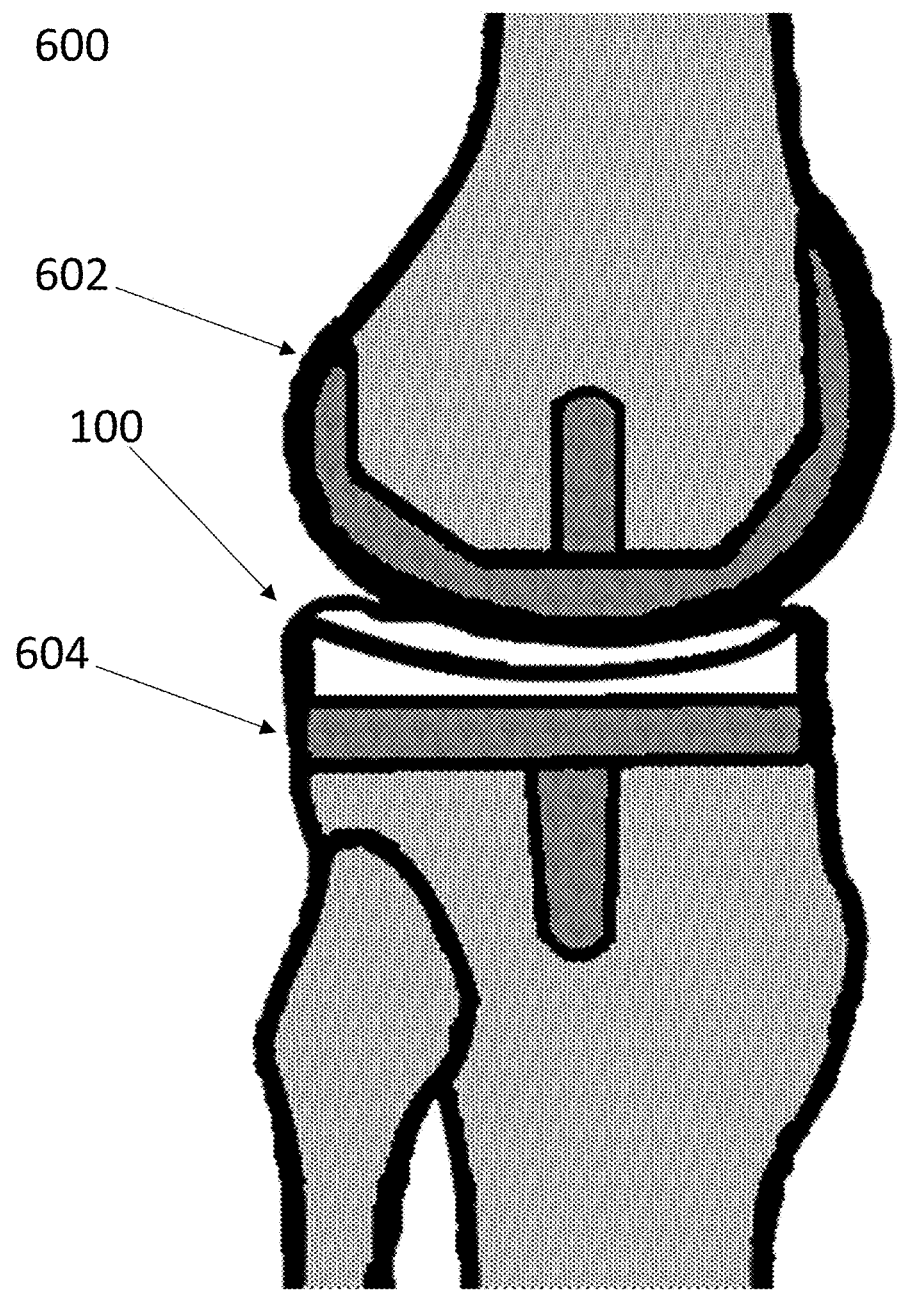
FIG. 6 is an exemplary embodiment of a total knee replacement prosthesis incorporating an antibiotic dispensing spacer.

Turning now to exemplary FIG. 6, an exemplary embodiment of a total knee replacement prosthesis 600 incorporating an antibiotic dispensing spacer 100 may be provided. Total knee replacement prosthesis 600 may have a femoral component 602, a tibial component 604, and a spacer 100, which may be an antibiotic dispensing spacer 100. According to an exemplary embodiment, spacer 100 may be connected to the tibial component 604; for example, the spacer 100 may slide onto the tibial component 604 and may lock at a locking mechanism. Alternatively, the spacer 100 and tibial component 604 may be connected by another mechanical connector or nonmechanical connection, or combination of connectors or connections, as desired. The femoral component 602 and spacer 100 may then articulate with each other, with the specifics of the articulation being dependent on the type of prosthesis used. For example, in a "posterior-stabilized" design, the tibial post of the spacer 100 may fit between the condyles of the femoral component in a rectangular box-like opening, and may slide back and forth in this opening as the tibial 604 and femoral 602 component rotate relative to one another. In another exemplary embodiment, such as in a "cruciate-retaining" prosthesis, the femoral component 602 may rest in and rotate on concave portions of the spacer 100, and may be constrained by the patient's own ligaments rather than a tibial post. In some exemplary embodiments, femoral component 602 and tibial component 604 may be constrained or hingedly connected to each other by a pin, or another mechanism, as desired.

The foregoing description and accompanying figures illustrate the principles, preferred embodiments and modes of operation of the invention. However, the invention should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments can be made by those skilled in the art without departing from the scope of the invention as defined by the following claims.

What is claimed is:

1. A spacer for a knee replacement prosthesis, comprising:
   a lower surface, the lower surface comprising a locking component adapted to couple with a tibial tray;
   an upper surface, the upper surface comprising a pair of condyle support platforms, each of the condyle support platforms being smooth, the surface of each of the condyle support platforms further having a shallow concavity; and
   a body, the body having a hollow outer portion surrounding an internal cavity, the material of the body being impermeable to fluid; the body further having a port comprising a channel formed of a flexible or fibrous material, the channel extending through the hollow outer portion of the body, and permitting the introduction of fluid through the port into the internal cavity after the spacer is in situ, wherein the fluid to flow into the effective knee space is at a predetermined rate.

2. The spacer of claim 1, wherein the lower surface is connected to the tibial tray by a nonmechanical connection.

3. The spacer of claim 2, wherein the nonmechanical connection is one of grout or bone cement.

4. The spacer of claim 1, wherein the lower surface couples with the tibial tray in a temporary fashion.

5. The spacer of claim 1, further comprising a central femoral guide on the upper surface.

6. The spacer of claim 1, wherein the internal cavity further comprises at least one of a reservoir, pump, and fluid restrictor.

7. The spacer of claim 1, wherein the channel further comprises a fluid flow regulation device.

8. A total knee prosthesis, comprising:
   a femoral component comprising a femoral stem adapted to be inserted in an intramedullary canal of a femur, and a pair of condyles;
   a tibial component comprising a tibial stem adapted to be inserted in an intramedullary canal of a tibia and connected to the femoral component, and comprising a tibial tray; and
   a spacer, the spacer comprising:
   a lower surface, the lower surface comprising a locking component adapted to interlock with the tibial tray;

an upper surface, the upper surface comprising a pair of condyle support platforms, each of the condyle support platforms being smooth, the surface of each of the condyle support platforms further having a shallow concavity; and a body, the body having a hollow outer portion surrounding an internal cavity, the material of the body being impermeable to fluid;

the body further having a port comprising a channel formed of a flexible or fibrous material, the channel extending through the hollow outer portion of the body, and permitting the introduction of fluid through the port into the internal cavity after the spacer is in situ and means for the fluid to flow into the effective knee space at a predetermined rate;

wherein the locking component of the spacer is connected to the tibial tray of the tibial component, and wherein each of the condyles of the femoral component is disposed in one of the condyle support platforms of the spacer.

9. The total knee prosthesis of claim 8, wherein the port permits introduction of fluid into the internal cavity prior to implantation of the total knee prosthesis.

10. The total knee prosthesis of claim 8, wherein the port permits introduction of fluid into the internal cavity following implantation of the total knee prosthesis.

\* \* \* \* \*